(12) United States Patent
Brady et al.

(10) Patent No.: US 8,500,910 B2
(45) Date of Patent: *Aug. 6, 2013

(54) MODIFICATION OF BIOMASS FOR EFFICIENT CONVERSION TO FUELS

(75) Inventors: Michael Brady, Studio City, CA (US); Dennis Stamires, Dana Point, CA (US); Paul O'Connor, Hoevelaken (NL)

(73) Assignee: KiOR, Inc., Pasadena, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/057,968

(22) PCT Filed: Dec. 22, 2009

(86) PCT No.: PCT/US2009/069232
§ 371 (c)(1),
(2), (4) Date: Jul. 11, 2011

(87) PCT Pub. No.: WO2010/075405
PCT Pub. Date: Jul. 1, 2010

(65) Prior Publication Data
US 2011/0256615 A1    Oct. 20, 2011

(51) Int. Cl.
| | | |
|---|---|---|
| *C08B 37/00* | (2006.01) | |
| *C10L 5/00* | (2006.01) | |
| *C13K 1/02* | (2006.01) | |
| *C07C 1/00* | (2006.01) | |
| *C07C 4/00* | (2006.01) | |
| *C10G 1/00* | (2006.01) | |

(52) U.S. Cl.
USPC ............... 127/36; 44/605; 127/37; 585/240; 585/241; 585/242

(58) Field of Classification Search
None
See application file for complete search history.

(56) References Cited

U.S. PATENT DOCUMENTS

| 102,665 | A * | 5/1870 | Douglas .................... 34/350 |
|---|---|---|---|
| 353,998 | A * | 12/1886 | Wheeler ..................... 201/30 |
| 1,831,105 | A * | 11/1931 | Fairley ....................... 585/355 |
| 1,845,917 | A * | 2/1932 | Howard ...................... 201/20 |
| 4,344,770 | A * | 8/1982 | Capener et al. ............ 44/388 |
| 4,670,613 | A | 6/1987 | Ruyter et al. |
| 4,797,135 | A * | 1/1989 | Kubat et al. ................ 44/500 |
| 5,605,551 | A * | 2/1997 | Scott et al. ................. 44/307 |
| 2004/0034262 | A1 * | 2/2004 | Van de Beld et al. ......... 585/240 |
| 2009/0090046 | A1 * | 4/2009 | O'Connor et al. ............. 44/307 |
| 2010/0181183 | A1 * | 7/2010 | Koukios ...................... 201/2.5 |
| 2010/0209965 | A1 * | 8/2010 | O'Connor et al. ............. 435/41 |
| 2010/0270499 | A1 | 10/2010 | Fang et al. |
| 2011/0154720 | A1 * | 6/2011 | Bartek et al. ................. 44/307 |
| 2012/0022307 | A1 * | 1/2012 | Yanik et al. .................. 585/240 |

FOREIGN PATENT DOCUMENTS

| CN | 101235095 | 8/2009 |
|---|---|---|
| EP | 0204354 | 12/1986 |
| EP | 0204354 | 5/1990 |
| EP | 1719811 | 11/2006 |
| EP | 1719811 A1 * | 11/2006 |
| WO | WO 2007009463 A2 * | 1/2007 |

OTHER PUBLICATIONS

Magara et al.; Wood Research; No. 76, pp. 1-9; 1989.*
Mantanis et al.; Swelling of Wood Part II, Holzforschung; vol. 48, No. 6, pp. 480-490; 1994.*
International Search Report (ISR) for PCT Application No. PCT/US2009/069232 (Publication No. WO 2010/075405), filed Dec. 22, 2009; ISR dated Mar. 9, 2010.
Kengo Magara, Jun-Ichi Azuma, and Tetsuo Koshijima; Microwave-Irradiation of Lignocellulosic Materials X; Report IX: Mokuzai Gakkaishi; Aug. 31, 1989; pp. 1-9; Research Section of Wood Chemistry, Department of Agriculture, Kyoto University.
George I. Mantanis, Raymond A. Young, and Roger M. Rowell; Swelling of Wood, Part II. Swelling in Organic Liquids; 1994; Department of Forestry, University of Wisconsin and USDA Forest Products Laboratory, Madison, USA.
Nathan Mosier, Charles Wyman, Bruce Dale, Richard Elander, Y.Y. Lee, Mark Holtzapple, and Michael Ladisch; Features of Promising Technologies for Pretreatment of Lignocellulosic Biomass; Bioresource Technology 96; Sep. 29, 2004; Laboratory of Renewable Resources Engineering, Department of Agricultural and Biological Engineering, Purdue University, West Lafayett, IN.
Parveen Kumar, Diane M. Barrett, Mchael J. Delwiche, and Pieter Stroeve; Methods for Pretreatment of Lignocellulosic Biomass for Efficient Hydrolysis and Biofuel Production; ASC Publications; Mar. 20, 2009; Industrial & Engineering Chemical Research.
Chinese Office Action dated Jan. 25, 2013 for co-pending Chinese Patent Appllication No. 200980152928.9; Applicant: KiOR, Inc.; Applicant Date: December 22, 2009; 18 pages.

* cited by examiner

*Primary Examiner* — Guinever Gregorio
(74) *Attorney, Agent, or Firm* — Hovey Williams LLP

(57) ABSTRACT

A process is disclosed for preparing biomass particles for thermolytic or enzymatic conversion whereby the biomass particles baying a moisture content of at least 20% are subjected to flash heating. The flash heating may be preceded by one or more adsorption/desorption cycles with water or steam. A swelling aid may be added during the adsorption part of an adsorption/desorption cycle.

13 Claims, No Drawings

MODIFICATION OF BIOMASS FOR EFFICIENT CONVERSION TO FUELS

BACKGROUND OF THE INVENTION

1. Field of the Invention

The invention relates generally to a process for making biomass material, in particular lignocellulosic biomass material, more accessible to subsequent chemical or enzymatic treatment.

2. Description of the Related Art

World energy demand is projected to increase substantially due to: increase in population growth; improvement of the standard of living in underdeveloped countries; and due to depletion of the reserves of fossil fuels.

Now, generally recognized by major countries, global climatic changes caused by increasing emissions of greenhouse gases, in particular $CO_2$ require that newly developed energy sources must be environmentally compatible and sustainable. Therefore, greener sources of energy are needed to replace or reduce the consumption of fossil fuels. Biomass is a source of a sustainable and renewable fuel, with potentially a net zero greenhouse gas impact.

To be usable as a fuel biomass needs to be converted. Biomass conversion technologies include biological processes, such as anaerobic or aerobic digestion fermentation, and thermal conversion processes, such as direct combustion for heating and generating electricity, gasification for producing syngas, and pyrolysis for producing bio-oils for use as fuels and as a feedstock for producing chemicals.

The thermal conversion processes also include hydrothermal processes, wherein biomass is treated in slurry form in autoclaves at temperatures above 200° C. and under autogenous pressures.

Pyrolysis processes have high potential for large scale commercialization as they provide flexibility in varying process conditions, such as heating rate, temperature, pressure, contact time, atmosphere, etc., to optimize yields of liquids (oil), gas and char. Of particular interest is fast (or flash) pyrolysis, designed to convert the biomass to maximum amounts of oil, employing a very low residence time, a very high heating rate and temperatures close to 500° C.

The oil produced in biomass pyrolysis has a high energy density that can be directly used in combustion or refined to fuels and specialty chemicals.

However, the pyrolysis derived bio-oils, because of their high oxygen contents, high viscosity, acidity, corrosiveness and low stability, have limited direct applications as fuels. Intensive research is being carried out to upgrade the quality of said bio-oils to products that are comparable to conventional fuels in composition, chemical and physical properties.

The pretreatment processes of biomass before pyrolysis offer possible solutions in biomass modification that will allow the pyrolysis process to be conducted at less severe conditions (i.e., lower temperatures, shorter contact times), and more efficiently to the extent that more oil is produced and of better quality.

Biomass conversion in large commercial plants is now carried out to produce ethanol, primarily using as feeds renewable sources such as corn, sugar cane, and cereal grains. Because the cost of these raw materials represents roughly one-half of the total cost of the process to produce the ethanol, it is of paramount interest to use cheaper biomass raw materials for conversion to ethanol. Furthermore, it is important to utilize other biomass sources other than grains in order to minimize the impact on food prices.

Consequently, less costly lignocellulosic biomass materials derived from agricultural and forestry residues are very attractive for use as sources to be converted to ethanol or other fuels.

Ethanol has been produced from expensive raw materials, i.e., sugar cane, corn, starches, grains, cereals. However, there is need to use less expensive materials such as non-food lignocellulosic materials including grasses, municipal solid waste (MSW), wood wastes, forestry and agricultural wastes. However, the technologies known for handling the conversion of such raw materials efficiently to ethanol are limited, and different from those used commercially to convert the sugar cane, corn, grains and cereals.

Therefore, the objective of this invention is to develop economically feasible and environmentally friendly processes that will allow an efficient conversion of the non-food cellulosic raw materials to ethanol.

In general, although there are potentially many processes that can technically meet the conversion requirements, to be successful a process must also meet the economic and environmental requirements.

The use of ethanol in automobile fuels not only reduces the need for petroleum (crude oil), but also substantially reduces the carbon dioxide car-exhaust emissions.

Commercial large scale operations involving the production of ethanol from cellulosic biomass use biological or non-biological processes to depolymerize (break down) the cellulose. The most commonly used biological processes use enzymes, whereas the non-biological processes use an acid-hydrolysis to convert the cellulose to sugars, mostly using dilute or concentrated sulphuric acid. These processes are considered as a pretreatment of the biomass in the overall bioconversion processes, which are followed by fermentation and distillation.

in the prior art we find descriptions of other kinds of pretreatments such as steam-explosion, which is followed by enzymatic hydrolysis, fermentation and distillation in the production of ethanol (see C. E. Wyman et al, Bioresource Technology 96 (2005), 199-1966).

Since the presently known processes for conversion of the lignocellulosic biomass (derived from agricultural and forestry residues) are more expensive than the processes used now commercially to produce ethanol from grains and cereals, there is a strong interest in developing new or unproved processes that will allow a more cost-effective and environmentally acceptable manner of converting lignocellulosic biomass (from residues derived from agriculture and forestry materials) to ethanol.

In general, lignocellulosic biomass from such residues consists mainly of three components: cellulose, hemicellulose and lignin. The cellulose component is a polymer of glucose, formed in long strand units, associated with the hemicellulose component layer and both (the crystalline cellulose and hemicellulose) are encapsulated by the lignin.

In ethanol production of the bioconversion processes, the cellulose and hemicellulose are converted to sugars, such as glucose and xylose, followed by fermentation. Lignin is a 3-dimensional branched polyaromatic matrix acting as a sheath (like a protective coating) to the cellulose and hemicellulose components of the biomass.

As a result, due to the difference in the bonding of the components, the high crystallinity of cellulose and due to the protective sheath of the lignin, the penetration, interaction/reaction of the acids and/or the enzymes is highly impeded by the restricted access to the bulk of the biomass particles. This problem is much less present when cereal grains are processed to produce ethanol.

However, for biomass from non-cereal grain sources, the lignin present resists the enzyme attack and hence lower yields are obtained. To at least partly overcome this problem, pretreatment of the biomass is necessary prior to subjecting the biomass to enzymatic hydrolysis (see N. Mosier et al., Bioresource Technology 96 (2005), 673-686).

Since the major cost of the overall conversion process is due to the biomass feed and enzymes, it is necessary to minimize the use of enzymes and obtain the maximum conversion of the carbohydrates to ethanol.

Lignocellulosic biomass as a feedstock presents a large spectrum of compositions. The interactions between composition, structure and chemistry within the lignocellulosic material result in complex heterogeneous behavior towards the various pretreatment methods, and in variations of reactivity towards enzymatic digestibility. Specifically, the presence of three major components, that is, crystalline cellulose, hemicellulose and lignin, as well as their association in forming special composites, like the sheathing of cellulose by lignin, hydrogen bonding between the components, etc., contribute to the recalcitrant behavior of the raw lignocellulosic biomass.

To improve the reactivity of the raw biomass towards enzymatic digestion, several pretreatment technologies have been developed, aimed at eliminating the physico-chemical and mechanical barrier characteristics of the raw lignocellulosic biomass in order to enhance the penetration of enzymes into the bulk of the individual biomass particles to cause digestion and hydrolysis.

These pretreatment processes, known to the prior art, involve chemical, biological, physical/mechanical and combinations thereof.

For a pretreatment process to be effective for large-scale commercial operations, to be cost effective and environmentally acceptable, it should not require use of very small biomass particles, should preserve the hemicellulose, use a minimum amount of disposable materials, operate with low energy and labor requirements, minimize the formation of byproducts and degradation of products, utilize low-cost chemicals, and be capable of recycling the chemicals used in the process. Further, such pretreatment processes should require low-cost equipment, with low maintenance and operating costs.

For these reasons, a considerable amount of R&D work has been devoted during the last few years for developing means to pretreat the lignocellulosic biomass in such ways that the accessible bulk surface area increases, so that the raw biomass becomes more reactive to the enzymes, and more effective in producing mono- and oligosaccharides, which will allow an increase in the biomass ethanol conversion.

The most popular processes are acid and enzymatic hydrolysis processes, which are used mostly to convert the cellulose and hemicellulose to glucose.

In the prior art there are several versions of the original acid hydrolysis process. These involve either very concentrated acids or dilute acids in one or two step treatments, and combinations of acid treatment with steam treatments, such as steam-explosion.

Overall, the pretreatment processes utilizing acids, such as sulphuric acid, require specially constructed plant equipment that must be resistant to acid corrosion. Additionally, the use of acid requires neutralization by a low-cost base such as sodium hydroxide or calcium hydroxide, and the salts formed thereby must be filtered and washed from the biomass. This creates large waste streams that require disposal and lead to additional costs. Further, for the use of highly concentrated acids, the process requires an additional evaporator to produce/recycle the highly concentrated acid, and to handle large quantities of water used in the pretreatment and recovery.

The acid pretreatments of lignocellulosic biomass feeds used to convert the cellulose and hemicellulose to fermentable sugars have important disadvantages in the form of high costs, low efficiencies, and environmental problems. Specifically, the high acid concentration process has the additional disadvantages of corrosion of equipment and high cost waste stream disposal, whereas the dilute (low acid concentration) process produces a low and slow conversion of the biomass to fermentable sugars, and deactivation of the process by binding some of the enzymes to lignin.

Pretreatments using steaming (steam-explosion) as such and combinations with acid treatments also have certain disadvantages. During steam-explosion pretreatments, the pentoses and hexoses produced from the hydrolysis of the cellulose material are further, to some extent, convened to undesirable by-products such as furfural, levullinic and formic acids together with other products (see M. M. Wu et al, Appl. Biochemistry and Biotechnology 77 (1999) 47-54).

In general, processes involving acid treatments and steam-explosion produce compounds such as aliphatic acids, phenolic and furan derivatives. These degradation products act as inhibitors in subsequent processes using enzymes to convert the sugars to ethanol (see V. S. Chang, et al., Appl. Biochemistry and Biotechnology 84 (2000) 5-37).

Further, although high severity steam explosion allows the enzymes to react more effectively, it does degrade the produced sugars and reduces the yields, as well as making the lignin less reactive. Using less severe steaming-acid pretreatments produces lower glucose yields, since the enzymes cannot react with the major part of the cellulosic material (see J. Soderstrom, et al., Biomass and Bioenergy 24 (2003), 475-486; U.S. Pat. No. 4,880,473 and U.S. Pat. No. 6,692,578, U.S. Patent Application US2005/0069998A1, U.S. Pat. No. 5,597,714, WO2006/085762 A1).

In the prior art, there are other pretreatment processes described such as high pressure and temperatures in the range of 200° C. to 250° C. pretreatments. These conditions require special high pressure equipment which is costly and difficult to operate on a large scale commercially. Additionally, the cooking of biomass at such high temperatures and pressures produces excessive amounts of aldehydes, which inhibit the digestion process of the enzymes with the biomass.

Other pretreatments known in the prior art involve the use of sodium hydroxide and calcium oxide/hydroxide in dilate slurry forms, or under pressure and in air or in oxygen atmospheres. This requires processing taking several hours or several days. Overall, the processing of slurries requires large volume equipment, washing and filtration steps. Additionally, processing with lime produces non-recoverable salts as being occluded in the bulk of the biomass.

Other pretreatment processes described in the prior art involve the use of ammonia in liquid or gaseous form to treat the biomass.

The Ammonia Fiber Explosion (AFEX) process involves pressurized absorption of ammonia by biomass, followed by low pressure desorption that explosively erupts the biomass lignocellulosic matrix. A similar process is the ammonia-freeze explosion pretreatment. These processes need specialized equipment to handle the biomass, which must be agitated while it is exposed to high pressure ammonia gas, and subsequently exposed to a low pressure/vacuum condition to desorb ammonia. The overall process requires special equipment to handle the high ammonia pressure and vacuum conditions as well as recover, recompress, and recycle the ammonia.

This process in small scale operations produces pretreated herbaceous and non-woody agricultural biomass materials that have good enzymatic conversion yields. With forestry-derived and other hard and woody (lignin-rich) biomass materials the ammonia pretreatment process has not been successful. Moreover, the overall costs in equipment and process operation are substantially high.

Enzymatic hydrolysis presents a promising process for large-scale operations using lignocellulosic biomass, as it is not energy intensive, environmentally compatible and does not require the use of corrosive chemicals.

The main disadvantage of this process has been the cost of producing the enzymes, although during, the most recent years, with new improved processes, this cost has been reduced (see V. S. Chang et al., Applied Biochemistry and Biotechnology 84 (2000) 5-37).

It can be concluded that there is need for developing pretreatment processes that allow the maximum conversion of lignocellulosic biomass to ethanol via high yield enzymatic hydrolysis, without the use of corrosive chemicals, waste streams and specialty high-cost equipment.

Such processes will produce high yields of fermentable sugars from lignocellulosic feedstocks and in an environmentally acceptable manner and will be carried out commercially at comparable costs to the presently used petroleum-derived fuels, and can be used as replacements.

In general, any pretreatment of the lignocellulosic biomass particles to enhance its conversion must at least increase the micro- and macro-accessibility to the bulk of the particles, allowing penetration of the enzymes and chemicals. The enzymatic degradation and digestion of cellulosic materials constitutes the key process of the natural carbon cycle.

Overall, in view of the fast increasing prices of cellulosic biomass materials used in food products and now with limited availability, there is an increasing need to develop cost effective processes that will enable to convert, cost effectively, biomass materials that are not used in food products, for ethanol production. As the most popular existing pretreatment process presently available are only suitable for applications using biomass feeds derived from biomass materials that are used in food products, there is a much greater need to develop new pretreatment processes that are effective in improving the ethanol yields from processing less costly feeds such as the woody types, using smaller amounts of enzymes and less costly plant equipment, chemicals and overall processing.

In the prior art, the term cellulases is used to describe a class of enzymes responsible for the biodegradation natural process. Cellulases are mainly produced by bacteria and fungi. For the purpose of this discussion, it is noted that the proteinic conveyors of the complex enzyme groups have molecular weights in the region of 30,000 to 100,000, and have globular shapes with hydrodynamic diameters in the range of 3 to 4 nm. Therefore, the openings of the cannulae, pores, cavities and interfibrillar interstices, must be large enough to allow molecules, ions, compounds, and enzymes to penetrate in the bulk of biomass. For an efficient enzymatic digestion and conversion, the biomass particle should have the largest possible number of such openings with diameters at least 3 to 4 nm (H. A. Kzassig et al, in Polymer Monographs, "Cellulose", vol. 11 (1993) p 202).

This invention is based on optimizing and utilizing a very basic property of lignocellulosic materials (like woods) which is the swelling which is caused by organic and inorganic liquids like water. Although this property of woods is a disadvantage for applications in construction, boards or packaging, etc., to the contrary, the swelling property of woods and other lignocellulosic materials is very useful for the enzymatic conversion of such lignocellulosic materials to ethanol (Mentanis G., et al., Wood Sci. Technol. (1994), 28, 119-134, F. F. Wangaard, et al., Wood Sri. Technol. (1967) 1,253-277).

This invention involves optimizing the water swelling process to affect penetration in the intercrystalline regions reached through pores and capillaries leading into the interfibrillar spaces.

In particular, the objective of this invention is to provide conditions and the materials that cause optimum swelling that increases the accessibility and reactivity. Such optimum swelling involves both intrafibrillar and intercrystalline water penetration.

To increase the penetration of water to achieve maximum bulking or swelling, solutions of salts, acids, bases and organic water soluble compounds can be used, and preferably salts or inorganic bases. The paths that the water and solute molecules follow on their way into the bulk of the biomass involve the existing structural pores, capillaries and voids between fibrillar elements.

While water molecules penetrate into the interior of the biomass, they are causing disruption of fibrillar associations and move into regions interlinking the crystallite ensembles forming the fibrils (A. Stamm, Ind. Eng. Chem. Vol. 27, No. 4 (1935) 401-406).

Deeper penetrations which require more severe process conditions and higher solute concentrations, involve the penetration of water molecules into the lattice structure of the crystallites, causing rupture of the hydrogen bonded layers and creation of accessible and reactive internal surfaces. The strong interaction of water and, for example, a strong inorganic base with the biomass, results in the opening of the intraplanar and interplanar hydrogen bonded links that cause lattice transformation, which in turn allows solute molecules/ions to diffuse between lattice layers. Usually, the swelling or bulking of the lignocellulosic materials (i.e., woody kinds) by liquids causes corresponding changes in the dimensions of the wood panicles. However, the changes, if any, in the dimensions of the particles do not necessarily reflect the amount of solvent sorbed in the bulk of the particle. This is due to existence of fine and coarse capillaries within the bulk structure, that attract ionic solvents (e.g., water) to fill the available space without causing measurable changes in the dimensions of the lignocellulosic mass.

The effectiveness of the solvent to cause swelling depends primarily on its basicity, hydrogen bonding affinity and molecular bonding. The swelling properties of lignocellulosic materials (such as wood), and the ability of different chemicals to cause swelling has been studied for over 70 years (A. Stamm, Ind. Eng. Chem. vol. 27, No. 4, 1934). Briefly, it has been shown that the extent of swelling and solvent sorption can be related to the hydrogen bonding affinity of the solvent.

A simple model of the mechanism of the swelling process of wood with water involves the penetration of water molecules via capillaries into the bulk structure, wherein the water molecules first interact with the hydrogen-bonded hydroxyl groups of the lignocellulosic mass to form a transition-state, that is, an energetically unstable state, which dissociates to a water for solvent) molecule and becomes hydrogen-bonded to the lignocellulosic mass. Thus, this mechanism is based on a chemically activated process following the Arrhenius equation, characteristic of classical chemical reactions involving an activation energy.

Accordingly, the rate and extent of swelling substantially increases with increasing temperature. The interaction of water with the biomass that causes bulking (swelling) and at the same time creates accessibility, can be increased by the presence in the water of certain soluble salts, which cause substantially more swelling (A. Stamm, Ind. Eng. Chem. vol. 27, No. 4, 1934).

The "activity" of certain salts to increase swelling is in the following order:
Cations: K<$NH_4$<Na<Ba<Mn<Mg<Ca<Li<Zn and
Anions: $ClO_3$<$SO_4$<$NO_3$<Cl<Br<$ClO_4$<I<CNS However, there are exceptions to this order, depending on concentrations, temperature and kind of biomass used. In general, much more swelling occurs in alkaline solutions than in acidic solutions.

Certain salts (like concentrated $ZnCl_2$) used in hot solutions to cause swelling, react much further by splitting fibrillar aggregates and even dissolving parts of the biomass (Penn, W. S. (1949) Elec. Manuf. 5, (1), 8).

Bases, both organic and inorganic, have much more of an affinity to interact with biomass materials. According to one theory, cellulosic materials can be considered to exhibit chemical properties similar to mono-basic acids, which can be neutralized by contacting the biomass with strong bases.

In general, the affinity of certain bases to cause swelling for cellulosic materials can classified in the following order: LiOH>NaOH>KOH>RbOH>CsOH (See K. E. Cabradilla and S. H. Zeronian, "Influence of Crystallinity on the Thermal Properties" in Thermal Uses and Properties of Carbohydrates and Lignins, Academic Press (1976)).

Briefly, and for the purpose of this invention, the action of water or other polar solvents and when enhanced by soluble salts bases or acids, but preferably with strong bases, and conducted at optimum temperature, concentration and pH result, to different extents, in the following:

Rupture of hydrogen bonds that hold together fibril aggregates, thereby creating more reactive bulk surface areas.

Breaking of intraplanar and interplanar hydrogen bonds, allowing different biomass components to move, dissolve or rearrange as well as allow the soluble (salt) ions to penetrate to the interior of the biomass.

As a result of these chemical interactions, the bulk is transformed to a sponge-like structure. The swelling enlarges the pores and capillaries with exits to the surface, as well as opening of interfibrillar spaces, such that the biomass becomes accessible for reactions with chemical compounds, salt, acids, bases, as well as enzymes.

Biomass swollen with polar liquids like water, when it is subsequently dried at relatively low temperatures (at 80-100° C.), does not allow all liquid present in the swollen regions to escape. This entrapment of the swelling agents and/or present solutes, like salts, is accompanied by some shrinkage of the biomass particles. Consequently, the swelling process followed with a drying step to entrap (encapsulate) chemical compounds, which may form inclusion complexes within the pores, voids, capillaries, interfibrillar interstices, provides means to activate the biomass in a way that the biomass becomes more reactive in the enzymatic conversion, as well as to thermal and hydrothermal conversion for the production of fuels.

In general, lignocellulosic biomass, depending on its origin, contains, besides cellulose, hemicellulose and lignin, other components such as resins, tannins, terpenes, fats, etc. These materials are referred to as "extractives," as they can be removed by (organic) solvents, such as alcohols. Additionally, the lignocellulosic biomass, depending on its kind and origin, contain a variety of metals. Mild treatments, like hot water (60-90° C.) can remove most of these "extractives" without altering the cellulosic components of the biomass. In general, the removal of "extractives" results in increasing the rate of diffusion of the solvent and solutes into the biomass, while increasing the size of the capillaries, disrupting the cell wall structure, and decreasing the network of secondary hydrogen bonds. Thus, the internal structure of the cell wall loses stability and increases the reactivity of the exposed surfaces towards the solvent/solute molecules. Therefore, removal of the "extractives" increases the rate of swelling, and its amount (G. Mantanis et al., Holzforschung, 49 (1995) 239-248; WO 00/74909 A1).

Lignocellulosic biomass, besides the organic extractive components, contains also inorganic extractives. About 20 kinds of metals have been identified in various kinds of lignocellulosic biomass, which vary not only with the kind of biomass, but also with its origin.

In general, depending on the source of the biomass, its history of growth, location, etc., about 20 inorganic species have been found to be present in different kinds of biomass, with the most abundant being Na, K, Ca, Mg, S, Si, Fe, Mn, Al, P. In some biomass sources, the total concentration of inorganic species can reach 25% based on dry weight of the biomass.

Thus, there is a particular need for processes that prepare non-food biomass materials, in particular lignocellulosic biomass materials, for subsequent enzymatic or chemical conversion to liquid fuels.

BRIEF SUMMARY OF THE INVENTION

The present invention addresses these problems by providing a process for opening up the structure of a biomass material, said process comprising the steps of:
(i) providing biomass particles having a moisture content of at least 20 wt. %
(ii) subjecting the biomass particles to flash heating.

Optionally the biomass particles are subjected to a pretreatment step. The process including the optional pretreatment step can be exemplified as follows: in the First step of the process lignocellulosic biomass in the form of powder, chips, granules, etc., is treated in a kneader at a temperatures near 100° C., in the presence of water or in an aqueous solution of a salt, an acid, or a base solution, such that sufficient water or aqueous solution is sorbed by the biomass.

After this pretreatment, the biomass with the sorbed water can be processed in an extruder or filter press wherein water is squeezed out. Optionally the biomass coming out of the extruder or filter press can be returned to the kneader for another cycle of water sorption and then again passed through the extruder or filter press. The water squeezed out from the extruder or filter press contains the extractives which are both organic and inorganic.

Another option involves the removal of some of the extractives in one or more "sorption-desorption" cycles, and finally in the final sorption cycle to use water soluble inorganic additives such as salts, acids or bases which may enhance subsequent conversion processes to produce bio-oils, syngases, or ethanol.

One or more of the "sorption-desorption" cycles may be conducted using an alkaline water solution such as sodium hydroxide, or using an acidic water solutions such as sulfuric, nitric or hydrochloric acids that enhance the removal of metals from biomass and also hydrolysis of the components, all resulting in creating larger internal surface area and volume, making the biomass more accessible to enzyme digestion or to chemical reactions.

The second step of the process causes an instant sorbed water flash-vaporization, which results in rapid vapor pressure increase that bursts and ruptures the compacted fiber structure of the biomass particle, thus creating larger voids, internal volume and surface area as well as destroying hydrogen bonding between individual components, thus exposing them to external chemical reactions, which include enzymatic digestion and hydrolysis and reactions with acids and bases.

It is advantageous to combine the flash vaporization with a precipitous pressure reduction, so as to further increase the explosive forces exerted on the biomass structure. Such a pressure drop may be effected by opening a valve to a vacuum source. Conveniently, the vacuum source may comprise a buffer vessel having a large volume, so that the vacuum source can cope with the sudden supply of gases and vapors. The vessel containing the biomass material may be provided with a gas/solid separator, such as a cyclone, to prevent the particulate material from being sucked into the vacuum source.

An alternate way of effecting a precipitous pressure drop makes use of the Bernoulli effect. The biomass material is taken up by a lift gas, and transported at a high rate of flow through a tube system. The tube system is provided with a restriction having a significantly smaller diameter than the upstream and downstream portions of the tube system. As the lift gas is being forced through the restriction, the flow rate accelerates, and the pressure drops.

Additionally, the modified biomass produced in the second step is more reactive towards hydrothermal and thermoconversions, such as pyrolysis, gasification and combustion. In particular, in pyrolytic reactions, the so modified biomass, due to its larger bulk porosity, allows the formed gases and condensable vapors (oils) to escape faster and with a smaller amount of bulk entrapment; thus higher yields of oils and gases can be produced in commercial pyrolysis and gasification operation, with minimum amounts of residues (chars).

There are cases in pyrolysis and gasification of biomass conversion wherein the addition of inorganic additives enhances some of the product yields and the selectively. For example, lime added to biomass enhances the gasification process. In such processes lime has been physically mixed with the biomass feed. However, the effect of the lime can be further enhanced using the process of this invention that allows the lime to be "in-planted" in the bulk of the biomass particle. For example, in the first step of the process of this invention, lime, or other inorganic salts, such salts of the alkaline or alkaline earth metals, are introduced in the water used to be sorbed by the biomass during kneading. Subsequently, the biomass, having sorbed the water solution containing the metal salt(s), is processed in the second step of this invention wherein the flash (rapid) sorbed water vaporization allows the water vapor (steam) to escape while it ruptures the bulk of the biomass particle and at the same time while it vaporizes, deposits uniformly the metals on the internal surface of the particles. Therefore, the metal(s) in the product of the second step are uniformly distributed within the bulk and are in close contact with the three biomass components, i.e., the lignin, hemicellulose and cellulose. Thus, all three components are present in a highly porous composite with increased accessibility to penetration of chemicals from outside environments into the interior of the particle, as well as having larger exit channels, voids, etc., that allow a faster and unhindered diffusion and exit of vapors/gases/liquids produced in the bulk, as, for example, in pyrolysis and gasification biomass conversion processes.

In another embodiment, the swollen biomass containing water or a solution, is coated with an inorganic material such as a catalyst, and subsequently is dried to fix the inorganic coating onto the biomass particle. This process is followed by heating the dried/coated biomass particles by a rapid/flash heating technique described in this invention to cause the internal vapors/gases to explode.

DETAILED DESCRIPTION OF THE INVENTION

We have discovered that when the swollen biomass particles prepared as described above are exposed to sudden rapid heating, or flash-heating, the sorbed water in the bulk of the biomass undergoes sudden vaporization that results in rapidly increasing the internal vapor pressure, thereby causing structural disruption in the bulk of the particle. This "in-situ" high pressure steam formation in the process of rupturing the compact arrangement of the fibrils also reduces the hydrogen bonding in regions of component interactions, thereby creating more internal surface area, larger pores and channels and increased accessibility to the interior of the biomass particle. Therefore, the increase of the internal openings and of the accessibility results in transforming the biomass material to a more porous and reactive form, allowing the enzymes to enter the bulk of the mass of the particle and hence produce higher yields of enzymatic conversion to sugars and ethanol.

Suitable plant equipment to conduct the process is available commercially for large scale operations, and this includes such equipment as flash dryers. AC-heaters, microwave ovens, tornado/cyclone-type high temperature dryers, etc.

The Process

The preferred process of the invention, including the optional pretreatment step, will be described as a "two-step" process.

The First Step.

In the first step the biomass, in powder, granules, chips, or in any other particulate form, is treated in a mechanical mixer such as a kneader, mix-muller or ball-mill, in the presence of water to cause the water sorption by the biomass. Treatments using a kneader or a mix muller are preferred in this invention, as both kinds of mixing machines have capabilities to heat the biomass while it is sorbing the water.

As the sorption rate and sorption capacity of the different kinds of biomass vary, the sorption conditions need to be adjusted to achieve the optimum of water sorption. Therefore, residence, time and temperature can be different depending on the water sorbing properties of the treated biomass. To aid the sorption in terms of rate and capacity, sorption aids or swelling aids ma be added to the water or to the biomass while it is treated in the mixing device.

A preferred sorption additive is an inorganic base, such as, but not limited to, a hydroxide, carbonate or hydroxyl carbonate of the alkaline and alkaline earth metals.

The swelling aid can comprise at least one cation from the group consisting of K; $NH_4$; Na; Ba; Mn; Mg; Ca; Li; Zn; Al. The swelling aid can also comprise at least one anion from the group consisting of $ClO_3$; $SO_4$; $SO_3$; $NO_3$; Cl; Br; $ClO_4$; I; CNS; $HSO_4$; OH; $HCO_3$; $HSO_3$; $(OH)CO_3$; and aluminate.

For certain biomass materials containing, relatively high concentrations of indigenous metals, which adversely affect the enzymatic digestion/hydrolysis processes, the first step of this invention is used to extract most of the metals from the biomass feed.

Operating in this mode, the sorption of the first step is conducted without addition of metal salts. However, if needed to enhance the metal extraction, the pH of the water can be increased above 7 by the addition of a base, preferably ammonium hydroxide or urea. The biomass can be treated, for example, in a kneader at temperatures from ambient to the boiling point of water.

The biomass having sorbed the water from the kneader is continuously fed to an extruder, centrifuge or to a filter press, where part of the sorbed water is squeezed out of the biomass. This squeezed-out water contains portions of the extracted metals. The biomass from the first metal extraction, coming, out from the extruder or filter press, can be returned into the kneader, where more water is added for another cycle of sorption to remove more metals, so the cycle is repeated.

In another variation of the operation of the first step, the first sorption step is conducted at pH above 7, and in the following step(s) the water sorption is done at pH below 7.

Therefore, low-cost lignocellulosic materials which contain organic extractives (resins, oil, tannins) as well as inorganic extraction (metal salts), can be used in the process of this invention.

In order to remove from the biomass both the organic and inorganic extractives, which all inhibit the enzymatic digestion/hydrolysis to form the sugars and the ethanol, the first/second cycles in sorption of water in the kneader can be done at an alkaline pH that enhances the removal of the organic extractives, and followed by the third/fourth sorption step which can be done at an acidic pH to enhance the removal of metal extractives. It is possible to employ a pH-Cycle-Swing between alternating acid/base pHs. Obviously, the order and number of cycles can be varied, and is done in a way to optimize the conditions to achieve the levels of metals acceptable to be present in the feed before the enzymatic conversion step.

The essence of the process conducted in this first step, that is, the sorption of water followed by "forced" desorption, all involving water in the liquid phase, can be envisioned as a kind of "Chimie-Douce" where the water enters the pores, cavities, capillaries of the biomass particles, dissolving some of the water-soluble extractives and subsequently is squeezed out of the biomass particles, carrying in it the soluble extractives. Said procedure can be repeated in order to achieve the degree of extractive removal desired.

Further, while this "Chimie-Douce" procedure operates and is removing, extractives from the surface and bulk of biomass particles, at the same time this ("cleansing") procedure creates more surface area, opens pores, channels, and overall increases the susceptibility of the biomass particles of enzyme digestion, chemical reactions, and so on.

Another variation of the mode of operation of the first step of this invention involves the use of a kneader or other mixing device which has an enclosed chamber, allowing it to heat the biomass at temperatures above 100° C. while the steam generated is kept within the kneader chamber.

Therefore, in the first step we perform a bulk-cleansing via the "Chimie-Douce" procedure, while at the same time more porosity and internal surface area is created.

The Second Step

In this step of the process, more internal surface area, larger pores, channels, voids, cannulae and openings to the bulk of the biomass particles are created, thus making the particle more accessible to enzymatic digestion, hydrolysis and to chemical reactions.

Specifically this step of the overall process involves heating the sorbed water present into the biomass particles rapidly to cause an in-situ flash heating (ie . . . vaporization) of the sorbed water that creates an instant internal high pressure that bursts (ruptures) apart the compact lignocellulosic particle structure, thus creating a large number and bigger openings to the bulk of the biomass particle.

The flash heating can comprise increasing the temperature from 90° C. or below, preferably 80° C. or below, to 110° C. or above, preferably 120° C. or above, in less than 30 seconds, preferably less than 10 seconds.

During the process of the particle bulk rupture and volume expansion, some hydrogen bonding between the components (i.e., cellulose, hemicellulose and lignin) is destroyed and possibly some rearrangement takes place as the lignin, under such severe hydrothermal conditions developed instantly in the bulk of the particle, becomes plastic and can rearrange its crystallographic location and its association with the cellulose and hemicellulose components. Accordingly, lignin renders itself to be accessible to chemical reactions and becomes easier to be removed by subsequent chemical treatments like, for example, acid leaching of the said treated biomass, to produce delignified cellulosic biomass materials.

Further, the biomass product obtained in this second step of the overall process can be recycled to the first step of the process wherein more indigenous metals can be removed and/or chemical catalysts additives, incorporated into the biomass particle.

Using the product of the second step of the overall process, which has more accessibility to the bulk of the biomass particles, recycled to the first step of the process, the water sorption is further facilitated and the removal or addition of chemical compounds into the bulk of the biomass particles is further enhanced.

Heating systems that can provide rapid heating in large scale commercial operations include flash dryers, microwave heating ovens, AC-heaters, tornado-type fluidized bed heaters, and so on. The dielectric heating is used commercially by radio frequency (Rf) heaters operating below 100 MHz, and microwave heating equipment operating at frequencies above 500 MHz. The biomass particles containing the sorbed water (being in swollen state) need to be rapidly heated to cause the instant sorbed water vaporization; however, the temperature and the heating time must be chosen so that the biomass itself does not start to become carbonized, or undergo oxidative surface reactions. The steam produced in the second step of the process can be condensed and the water recycled back to the first step of the process; otherwise, the steam can be used to provide heat to the first step of the process.

Thus, the invention has been described by reference to certain embodiments discussed above. It will be recognized that these embodiments are susceptible to various modifications and alternative forms well known to those of skill in the art.

Many modifications in addition to those described above may be made to the structures and techniques described herein without departing from the spirit and scope of the invention. Accordingly, although specific embodiments have been described, these are examples only and are not limiting upon the scope of the invention.

What is claimed is:

1. A process for converting biomass, said process comprising:
  (i) flash heating biomass particles having a moisture content of at least 20 wt. % to thereby provide modified biomass particles; and
  (ii) subjecting said modified biomass particles to pyrolysis, wherein said flash heating in step (i) comprises heating said biomass particles for less than 30 seconds, wherein said flash heating in step (i) comprises increasing the temperature from 90° C. or below to 110° C. or above, and wherein said flash heating in step (i) ruptures at least a portion of the lignocellulosic particle structure of said biomass particle.

2. The process of claim 1,
wherein step (i) is preceded by at least one absorption/desorption cycle wherein a liquid comprising water is absorbed into and desorbed from said biomass particles.

3. The process of claim 1 wherein the desorption part of the absorption/desorption cycle comprises squeezing water from the biomass particles in an extruder, centrifuge or a filter press.

4. The process of claim 1 wherein the moisture content of the biomass particles subjected to flash heating in step (i) is at least 30 wt. %.

5. The process of claim 1 wherein step (i) is preceded by contacting said biomass particles with water or steam.

6. The process of claim 1 wherein step (i) is preceded by mechanical treatment.

7. The process of claim 1 wherein step (i) is preceded by contacting the biomass particles with a swelling aid.

8. The process of claim 7 wherein the swelling aid is selected from the group consisting of water soluble bases, water soluble acids, water soluble salts, and mixtures thereof.

9. The process of claim 1 wherein the flash heating is carried out with radio frequency energy or microwave energy.

10. The process of claim 1 wherein the flash heating is followed by a pressure drop.

11. The process of claim 1 wherein the biomass particles are particles of a material selected from the group consisting of wood, grass, straw, bagasse, corn husks, citrus peels, algae, and mixtures thereof.

12. The process according to claim 1, wherein said pyrolysis is fast pyrolysis carried out in the presence of a catalyst.

13. The process according to claim 1, wherein said biomass particles comprise wood.

* * * * *